(12) United States Patent
Alijani et al.

(10) Patent No.: US 12,239,413 B2
(45) Date of Patent: Mar. 4, 2025

(54) 2D MATERIAL DETECTOR FOR ACTIVITY MONITORING OF SINGLE LIVING MICRO-ORGANISMS AND NANO-ORGANISMS

(71) Applicant: SOUNDCELL HOLDING B.V., 's-Gravenhage (NL)

(72) Inventors: Farbod Alijani, Delft (NL); Peter Gerard Steeneken, Delft (NL); Ireneusz Eugeniusz Roslon, Delft (NL); Aleksandre Japaridze, Delft (NL); Cornelis Dekker, Delft (NL)

(73) Assignee: SOUNDCELL HOLDING B.V., 's-Gravenhage (NL)

( * ) Notice: Subject to any disclaimer, the term of this patent is extended or adjusted under 35 U.S.C. 154(b) by 282 days.

(21) Appl. No.: 17/830,702

(22) Filed: Jun. 2, 2022

(65) Prior Publication Data

US 2022/0313091 A1    Oct. 6, 2022

Related U.S. Application Data

(63) Continuation of application No. PCT/NL2020/050621, filed on Oct. 8, 2020.

(30) Foreign Application Priority Data

Dec. 2, 2019   (NL) ..................................... 2024356

(51) Int. Cl.
| | | |
|---|---|---|
| *G01B 9/02015* | (2022.01) | |
| *A61B 5/00* | (2006.01) | |
| *C12Q 1/02* | (2006.01) | |
| *G01B 9/02091* | (2022.01) | |
| *G01N 29/02* | (2006.01) | |

(Continued)

(52) U.S. Cl.
CPC .............. *A61B 5/0066* (2013.01); *C12Q 1/02* (2013.01); *G01B 9/02027* (2013.01);
(Continued)

(58) Field of Classification Search
CPC .... A61B 5/0066; C12Q 1/02; G01B 9/02027; G01B 9/02091; G01N 29/022;
(Continued)

(56) References Cited

U.S. PATENT DOCUMENTS 9,810,683 B2 * 11/2017 Gimzewski ........ G02B 21/0056
10,203,331 B2 * 2/2019 Reed .................. G01B 9/02089
(Continued)

FOREIGN PATENT DOCUMENTS

| EP | 2348132 A1 * | 7/2011 | .......... C12Q 1/6825 |
| WO | WO-2020046191 A1 * | 3/2020 | ............ H01L 29/06 |
| WO | 2021112666 A1 | 6/2021 | |

OTHER PUBLICATIONS

I. W. Frank, D. M. Tanenbaum, A. M. van der Zande, P. L. McEuen; Mechanical properties of suspended graphene sheets. J. Vac. Sci. Technol. B Nov. 1, 2007; 25 (6): 2558-2561. https://doi.org/10.1116/1.2789446 (Year: 2007).*

(Continued)

*Primary Examiner* — Mohamed K Amara
*Assistant Examiner* — Noah J. Haney
(74) *Attorney, Agent, or Firm* — Peacock Law P.C.; Justin R. Muehlmeyer

(57) ABSTRACT

A motion detector adapted to detect activity of extremely small scale organisms, such as micro-organisms, bacteria and fungi, and even of viruses and genetic material, such as DNA and RNA. The motion detector is capable of detecting nano-motion, that is, motion in the order of nanometers or less.

20 Claims, 4 Drawing Sheets

(51) Int. Cl.
    *G01N 29/036*     (2006.01)
    *G01N 33/543*     (2006.01)

(52) U.S. Cl.
    CPC ....... *G01B 9/02091* (2013.01); *G01N 29/022* (2013.01); *G01N 29/036* (2013.01); *G01N 33/54373* (2013.01); *G01N 2291/02466* (2013.01); *G01N 2291/0255* (2013.01); *G01N 2291/0256* (2013.01)

(58) Field of Classification Search
    CPC ........... G01N 29/036; G01N 33/54373; G01N 2291/02466; G01N 2291/0255; G01N 2291/0256
    USPC ......................................................... 356/479
    See application file for complete search history.

(56) References Cited

U.S. PATENT DOCUMENTS

| | | | |
|---|---|---|---|
| 11,293,900 B2* | 4/2022 | Schlicke | G01N 29/4436 |
| 2005/0003396 A1* | 1/2005 | Ozkan | C12Q 1/6825 |
| | | | 435/7.1 |
| 2009/0124513 A1* | 5/2009 | Berg | G01N 29/022 |
| | | | 422/68.1 |
| 2016/0123973 A1* | 5/2016 | Cubukcu | G01N 27/4145 |
| | | | 438/49 |
| 2017/0045514 A1* | 2/2017 | Tao | G01N 33/56911 |
| 2017/0299537 A1* | 10/2017 | Swett | G01N 33/00 |
| 2018/0312898 A1 | 11/2018 | Kasas et al. | |
| 2019/0162662 A1* | 5/2019 | Raphael | G01N 21/554 |
| 2019/0376925 A1* | 12/2019 | Choi | G01N 33/48721 |
| 2020/0158712 A1* | 5/2020 | Branton | G01N 15/12 |

OTHER PUBLICATIONS

Kasas, Sandor, et al., "Detecting nanoscale vibrations as signature of life", PNAS, vol. 112, No. 2, 2015, 378-381.

Wang, Zenghui, et al., "Interferometric Motion Detection in Atomic Layer 2D Nanostructures: Visualizing Signal Transduction Efficiency and Optimization Pathways", Scientific Reports, vol. 6, Article 28923, 2016, 1-11.

* cited by examiner

2D MATERIAL DETECTOR FOR ACTIVITY MONITORING OF SINGLE LIVING MICRO-ORGANISMS AND NANO-ORGANISMS

CROSS-REFERENCE TO RELATED APPLICATIONS

This application is a continuation of International Patent Application No. PCT/NL2020/050621, titled "2D MATERIAL DETECTOR FOR ACTIVITY MONITORING OF SINGLE LIVING MICRO-ORGANISMS AND NANO-ORGANISMS", filed on Oct. 8, 2020, which claims priority to and the benefit of Netherland Patent Application No. 2024356, titled "2D MATERIAL DETECTOR FOR ACTIVITY MONITORING OF SINGLE LIVING MICRO-ORGANISMS AND NANO-ORGANISMS", filed on Dec. 2, 2019, and the specification and claims thereof are incorporated herein by reference.

BACKGROUND OF THE INVENTION

Field of the Invention

The present invention is in the field of a motion detector adapted to detect activity of extremely small-scale organisms, such as micro-organisms, such as bacteria and fungi, and even of viruses and genetic material, such as DNA and RNA. The motion detector is capable of detecting nano-motion, i.e. in the order of nanometers or less.

The present invention is in the field of motion detector adapted to detect micro- or nanometer motion of small-scale objects.

Techniques are available to detect cells and bacteria using micro- and nanosystems. These are however of limited use for biology, as they often destroy the live specimen, typically by requiring a vacuum environment. This limitation may pose a problem for advancement in further study and advancement in biology since it is not possible to look into processes that occur in live specimens, such as a metabolism thereof, growth thereof, and self-assembly and response to external stimuli or drugs.

Background Art

Motion detectors are typically provided with an oscillator. Recently detectors have been developed having a flexible sample support in the form of a cantilever, or an optical fiber, or a piezoelectric system, capable of fluctuating, such as in U.S. Pat. App. Pub. No. 2018/0312898. The displacement of the cantilever, typically flexing thereof, can be measured quite accurately using, for example, an optical system, typically comprising a mirror a laser, and photodiodes, which is capable of measuring a deflection of the cantilever. Movement detection is limited to a nanoscale or larger scale motion.

Traditional detectors and sensors, for certain applications, are not sensitive enough. Typically they cannot detect motion of a smaller living specimen, such as a single live bacterium or a virus. For certain application also a faster response is required such as revealing the status of the living organism in few seconds after a drug susceptibility test. Sometimes cost, size, multiplication, and complexity may be a challenge as well, in addition.

Discussion of any publications herein is given for more complete background and is not to be construed as an admission that such publications are prior art for patentability determination purposes.

The present invention relates to an improved two-dimensional (2D) motion detector, which solves one or more of the above problems and drawbacks of the prior art, providing reliable results, without jeopardizing functionality and advantages.

BRIEF SUMMARY OF THE INVENTION

It is an object of the invention to overcome one or more limitations of the prior art and provides a motion detector that is far more sensitive. The invention relates to a detector which can be used as a sensor, such as for metabolic activity of a sample, such as a single cell, a single bacterium, a single virus, or even a single biomolecule, by recording motion thereof. The detector comprises a suspended 2D material, e.g. a single layer of graphene, of $MoS_2$, of hexagonal-BN, or any other atomically thin material, which may be a heterogeneous material. On the suspended material layer said single living matter may be provided, at micro- or nanoscale attached to its surface or in close proximity of its surface. The measurement means may be one from the group comprising a Fabry-Perot interferometer, a Michelson or an optical interferometer, a laser Doppler vibrometer, or one or more capacitor electrodes cooperating with the 2D material as the opposite electrode of the capacitor, or an imaging system for measuring the position of the living matter on the suspended material. In other implementations the resistance of the 2D material (which can be chosen to be piezoresistive) is used to monitor activities of the living matter on top of the 2D material. The to be measured actuation of the sample is induced by the activity or fluctuations of the above single sample object of interest, changing physical/chemical properties of said suspended 2D material. The suspended material is carrying the living matter and typically also a solid, liquid, or viscous fluid that contains a controllable concentration of its favourable growth environment. The present detector may be used in methods to supply medicine, toxins, or radiation to the living matter and study the effect on their activity are described. It is found that motion of the said 2D material is directly related to the activity of the sample, such as the single living organism, that can in turn be used for, among others, drug susceptibility testing. This present detector may be used as stand-alone technology, that e.g. can make drug susceptibility testing available at point of care within seconds. It is particularly suited for life science and health applications.

The present detector is validated in laboratory tests typically using *E. coli* strains. In an example the detector was able to distinguish between living bacterium in a blank set-up, living bacterium being resistant to added antibiotic, and bacterium under stress (dying) being susceptible to added antibiotic (see below).

Below are some of the distinguishing features over the prior art, and effects thereof.

(i) The present sample receiver comprises a 2D material, like graphene, as the material on which living matter is suspended.

(ii) Graphene has been found to have a unique combination of properties, that makes it extremely sensitive for the intended activity monitoring applications: it is typically 1 atom thick, extremely flexible, it is an inert and carbonous material, that is compatible to biologic materials, and it is mechanically strong. Even very small forces between the living matter and the suspended graphene are found to lead to deformation of the graphene, because the material is in fact even more flexible than e.g. the cell membrane of the biological sample matter. It is this combination of properties that is unique for 2D materials and not known to be present in any other type of material.

(iii) The detector uses suspended 2D materials that can be fabricated in diameters of about 10 μm or less and thus potentially having sizes in the same order of the sample, such as the living organism.

(iv) The present detector is capable of detecting life of a single cell, a single bacterium, a single virus, or any single biomolecule. Current state of the art detectors are typically capable of detecting a multitude thereof, such as about 600-700 living species, such as on a flexible support like a cantilever.

(v) The present 2D material used for motion detection is virtually massless and has a very low stiffness (<0.1 N/m), Such supports performing very sensitive measurements at the single living micro- and nano-organism scale.

(vi) The present motion detector is at least about 100, and typically at least about 1000 times more sensitive than prior art detectors. It allows picometer motion detection, such as of the living micro- or nano-organism.

(vii) The motion detection may be performed in the presence of small, microliter volume, droplets, and typically in humidity chamber. It is therefore not much effected by liquid flow of a fluidic chamber.

(viii) With the present detector performing drug susceptibility tests at the level of single cells in a timeframe of few seconds are now possible.

(ix) It is also possible to create arrays of detectors, such as on a CMOS chip, that can be read out electronically, such as using a CMOS chip. The chip can measure resistance, capacitance, electrochemical signals, or other signals, that are responsive to the activity/motion of the living sample material, which is considered to influence motion of the suspended 2D material. CMOS electrodes and digital signal processing enables measuring a very large number of cells simultaneously. Also it can be used for creating different areas that are treated by different medicines.

(x) In one implementation of the invention, 2D material of different sizes and aspect ratios are put on the CMOS chips. Some of the said 2D materials being smaller than the living matter to be detected, some of them being larger. By studying the dependence of the motion on the size of the 2D material, information on the properties (size) of the living matter is obtained. E.g. 2D materials that cannot accommodate 1 single bacterium will move less than those that can. Steps in motion activity are also expected when 2, 3 or more bacteria fit on the 2D material.

Applications in healthcare centres, ranging from general practitioners to hospitals, are envisaged, as well as applications in biology, physics, and medical labs. As the invention is sensitive at the single cell level, only very small amounts of living matter are needed for its operation. For example, sample preparation times does not need multiplication (cell division) and cell culturing before making measurements. This enables use at the point of care (general practitioners) with analysis times in the order of 15 minutes. It enables precision medicine: e.g. a bacterial sample from a patient is put on a chip that contains an array of different medicines. Motion of the bacteria on each part of the chip is monitored. The medicine that kills the bacteria (where motion is seen to decrease and stop in time) will be used on the patient.

The present detector provides a way to probe the motion of a small sample, such as a single live organism, while being alive, without intervening in their natural physiology or behaviour. The technology is simple and cost efficient, such as a point-of-care testing technique for drug susceptibility, for preventing overuse of drugs, and for testing bacterial resistance to antibiotics. The inert and carbonous nature of graphene makes it ideally suitable for combining with organic living materials. The impermeability of the suspended graphene helps to make sure that the cavity below the said suspended material remains filled with air, such that the mechanical stiffness of the said suspended material stays low and sensitive to motion of the living matter. The mechanical strength of 2D materials like graphene ensures that the living material doesn't tear the material apart, despite its thin nature.

The present sensor assembly is dedicated for activity monitoring of a living microorganism or living nano-organism. The assembly is equally applicable to monitoring of other movement on nanoscale or picoscale. The sensor assembly comprises a 2D microscale motion detector, which is referred to as "microscale" as in plane dimensions thereof are in the low microscale, whereas a thickness typically is in the low nanoscale or even below a nm, the motion detector adapted to act as a sample receiver, such as for receiving the living organism, which organism may be provided in a liquid, such as in a droplet, comprising an inert suspended layer, onto which the living organism may be provided, and in view of the organism and optional liquid the layer is chemically and biologically inert, wherein the suspended layer is 1-5 atoms thick, at least one support for the suspended layer, which support may extend over the full boundary of the suspended layer, or may be provided at a part of the suspended layer, such as at two or more opposite edges, and a read-out system adapted for measuring alteration of the suspended layer. Therewith movement of e.g. the living organism over extremely small distances, or even of movement causing a centre of mass of the microorganism to shift, which may be in the order of picometers, can be measured accurately and reproducibly.

In a second aspect the present invention relates to a chip comprising at least one 2D microscale motion detector according to the invention. The present 2D microscale motion detector can easily be integrated into a chip, or any other micro-electronic structure, and can be integrated by using typically used semiconductor technology. Therein electrical connections, controls, and even micro-fluidic elements can be introduced simply. So the present invention also relates to an electronic device comprising a sensor assembly or chip according to the invention, and at least two channels each individually in electrical connection with the read-out system, such as 5-200 channels, at least one readout line.

In a third aspect, the present invention relates to a method for operating the sensor assembly according to the invention, comprising providing a volume of liquid, the volume being about <10 μl, preferably about <2 μl, such as <1 μl, the volume comprising a microorganism, or living cell constituent, or virus, and measuring motion of the microorganism, or living cell constituent, or virus, over time. Living cell constituents may relate to DNA, to RNA, to proteins, to enzymes, and so on, and fragments thereof, and combinations thereof. Also more than one organism, or cell constituent, or virus, can be measured accordingly. Examples of such measurements are given below.

In a fourth aspect the present invention relates to a disposable sample stage comprising a 2D microscale motion detector adapted to act as a sample receiver, comprising an inert suspended layer, wherein the suspended layer is about 1-5 atoms thick, and at least one support for the suspended layer, and typically also a substrate on which the support may be provided.

Advantages of the present description are detailed throughout the description.

In an exemplary embodiment of the present sensor assembly material of the suspended layer may be a two-dimensional crystal providing interlayer van der Waals interactions in a direction perpendicular to the layer surface, and is preferably selected from graphene, hexagonal-BN, black phosphorus, transition metal dichalcogenides, wherein the metal is preferably selected from Mo, W, Nb, and wherein the chalcogen is preferably selected from S, Se and Te, such as $MoS_2$, $NbSe_2$, and $WSe_2$, and combinations thereof.

In an exemplary embodiment of the present sensor assembly the read-out system may be selected from a Fabry-Perot interferometer, a Michelson interferometer, an optical interferometer, a laser Doppler vibrometer, one or more capacitor electrodes, a piezoelectrical element, a piezoresistive element, an impedance analyser, and combinations thereof.

In an exemplary embodiment of the present sensor assembly alteration of the suspended layer changes at least one physical characteristics thereof selected from deflection, resonance frequency, reflection spectrum, transmission spectrum, optical adsorption, orientation of at least part of the suspended layer, optical interference, 2D crystal structure, electromagnetic properties, such as resistivity, conductivity, and combinations thereof.

In an exemplary embodiment of the present sensor assembly the read-out system may comprise a laser for providing light, an optical system for directing light from the laser to the sample, an optical system for directing reflected light from the sample to a photo detector, such as a photo diode, optionally an amplifier for amplifying detected light response, and a recorder for representing motion, such as an oscilloscope.

In an exemplary embodiment of the present sensor assembly the suspended layer is about 1-3 atoms thick, such as 2 atoms thick. It is found that a response for a thinner layer is better.

In an exemplary embodiment of the present sensor assembly the suspended layer is about 0.1-50 μm wide, such as 1-2 μm wide.

In an exemplary embodiment of the present sensor assembly the suspended layer is about 0.1-50 μm broad, such as 1-2 μm broad.

In an exemplary embodiment of the present sensor assembly the suspended layer may have a stiffness of about <10 N/m, preferably about <3 N/m, more preferably about <1 N/m, even more preferably about <0.2 N/m, such as <0.1 N/m, and typically <0.01 N/m. The stiffness can be measured using an AFM or STM, applying a force (N) to the layer, and measuring the (vertical) displacement of the layer, at the position of the force.

In an exemplary embodiment of the present sensor assembly the suspended layer has a Youngs modulus of about >100 GPa, such as >500 GPa (ASTM E1111).

In an exemplary embodiment of the present sensor assembly the suspended layer has a weight of about $<10^{-15}$ kg, preferably about $<10^{-16}$ kg, such as $<10^{-17}$ kg. The very small weight has amongst others as advantage that very small movements, of otherwise also very light objects, such as microorganism, can be measured very accurately.

In an exemplary embodiment of the present sensor assembly under the suspended layer a cavity of about >100 nm height is provided, such as >250 nm, such as 1000 nm. Such sub-micrometre cavities can be provided using semi-conductor technology, such as by using a mask, and wet- or dry-etching. Very well dimensioned cavities can be provided thereby. The cavity may be fully surrounded by the substrate, the at least one support, and the suspended layer, or partly surrounded thereby, such as for 50-90% of its boundary area.

In an exemplary embodiment of the present sensor assembly the cavity may be filled with a fluid, such as a gas or liquid. The gas may be an inert gas, such as nitrogen or a noble gas, whereas the liquid may be water, or a physiologically acceptable fluid.

In an exemplary embodiment of the present sensor assembly, the at least one support comprises an electrically insulating material, such as with an electrical conductivity of about σ (20° C.) of $<10^{-3}$ S/m, preferably $<10^{-6}$ S/m, such as silicon oxide, silicon nitride, and silicon carbide. Therewith electrical connections and the like can be provided, being in contact with the detector, and further being insulated.

In an exemplary embodiment of the present sensor assembly the at least one support has a height of about 20-1000 nm, preferably about 100-500 nm, such as 200-300 nm.

In an exemplary embodiment of the present sensor assembly the at least one support may be provided on a substrate, such as a silicon substrate.

In an exemplary embodiment of the present sensor assembly the suspended layer, the at least one support, and substrate, are each individually non-toxic, and at least partly support organism activity, such as support appropriate cellular activity, including the facilitation of molecular and mechanical signalling systems, such as in order to optimise tissue regeneration, without eliciting any undesirable effects in those organisms, or inducing any undesirable local or systemic responses in the eventual host.

In an exemplary embodiment the present sensor assembly may further comprise a humidity chamber for receiving the suspended layer and a sample. Therewith controlled experiments can be performed, in a for the organism at least partly favourable environment.

In an exemplary embodiment the present sensor assembly may comprise an array of sample receivers, therewith providing the opportunity to perform a series of parallel and/or sequential experiments.

In an exemplary embodiment the present sensor assembly may comprise a chip, such as mentioned above.

In an exemplary embodiment of the present method, a chemical is added, wherein the chemical is preferably selected from pharmaceuticals or potential pharmaceuticals, such as anti-biotics, such as kanamycin, and chloramphenicol, and measuring a response of the microorganism, or living cell constituent, or virus, to the chemical over time. Examples thereof, and the response measured, are given below.

In an exemplary embodiment of the present method, the liquid comprises at least one of nutrition for the microorganism or for the living cell constituent or for the virus, a physiological liquid, and a metabolic support compound.

The invention will hereafter be further elucidated through the following examples which are exemplary and explanatory of nature and are not intended to be considered limiting of the invention. To the person skilled in the art it may be clear that many variants, being obvious or not, may be conceivable falling within the scope of protection, defined by the present claims.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings:

FIG. 4a shows motion of the suspended layer with adhered bacteria, FIG. 4b showing the motion after addition of Kanamycin antibiotic, FIG. 4c showing the motion after addition of Chloramphenicol, and FIG. 4d showing the variance of the time traces given in FIGS. 4a, 4b, 4c and 4d;

DETAILED DESCRIPTION OF THE INVENTION

The figures are detailed throughout the description, and specifically in the experimental section below.

Figure 1:
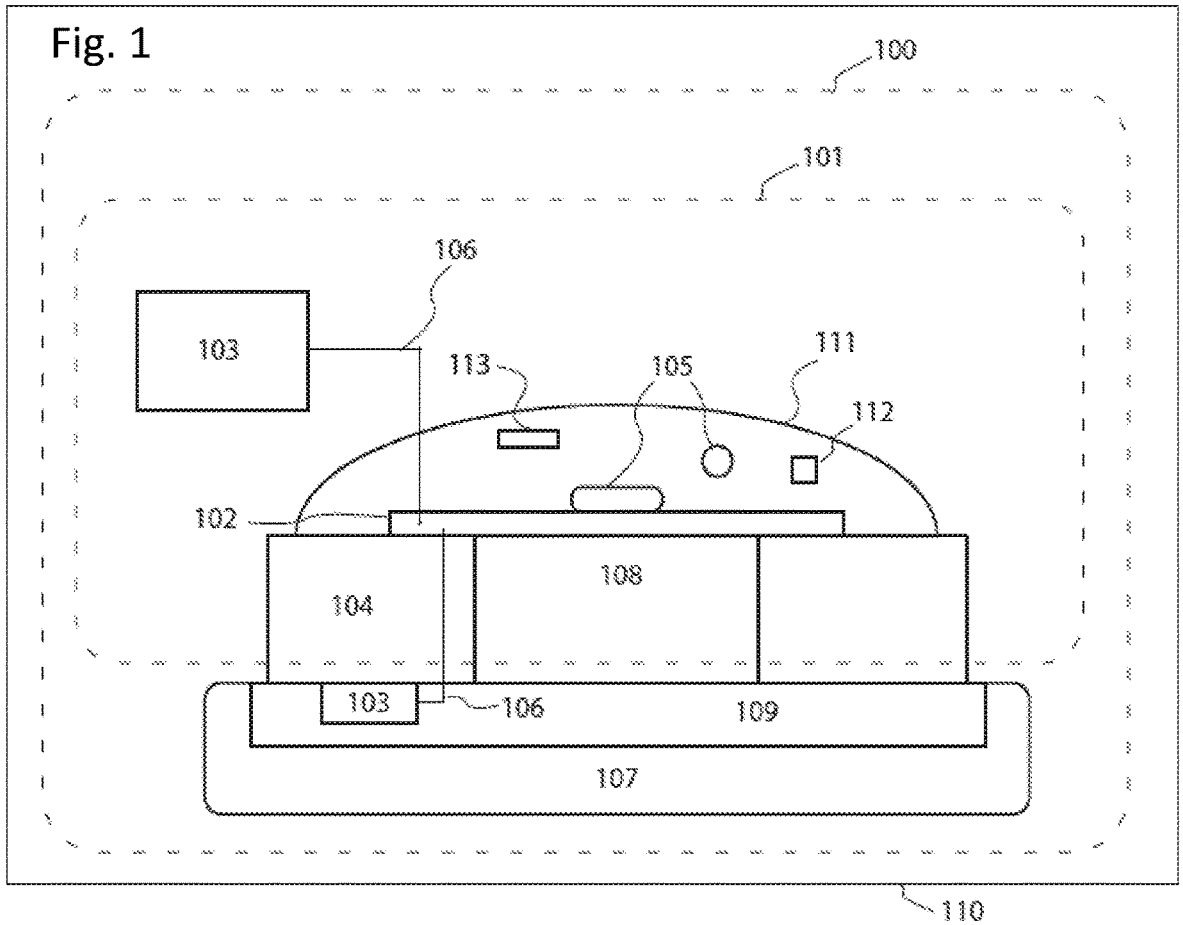
FIG. 1 is a schematic illustration of a sensor assembly according to an embodiment of the present invention.

In the figures the reference numbers represent the items mentioned thereafter:

- 100 sensor assembly
- 101 sample receiver
- 102 inert suspended layer
- 103 read-out
- 104 support
- 105 microorganism
- 106 channel
- 107 substrate
- 108 cavity
- 109 chip
- 110 electronic device
- 111 liquid
- 112 nutrition
- 113 chemical
- 115 optical components
- 116 humidity chamber
- 117 photo-diode
- 118 oscilloscope FIG. 1 shows the sensor assembly 100 comprising a sample receiver 101 with inert 2D material layer 102 acting as the motion detector. The 2D material is suspended over a cavity 108 using at least one support 104. Such geometry can be obtained using semiconductor technology, such as by using a mask, and wet- or dry-etching.

Turning back to FIG. 1, it is shown that the sensor assembly also comprises a chip 109 that sits on a substrate 107. The substrate 107 may comprise an array of sample receivers 101 on top of an electrical device 110.

In the embodiment of FIG. 1 also a liquid droplet 111 is dispensed on top of the sample receiver 101. The droplet contains micro-organisms 105 and nutrition 112. Chemicals 113 can be added to the droplet to change the behaviour of the micro-organism. The micro-organism can be also adhered to the 2D material and its motion can be probed by a read-out system 103.

Figure 2:
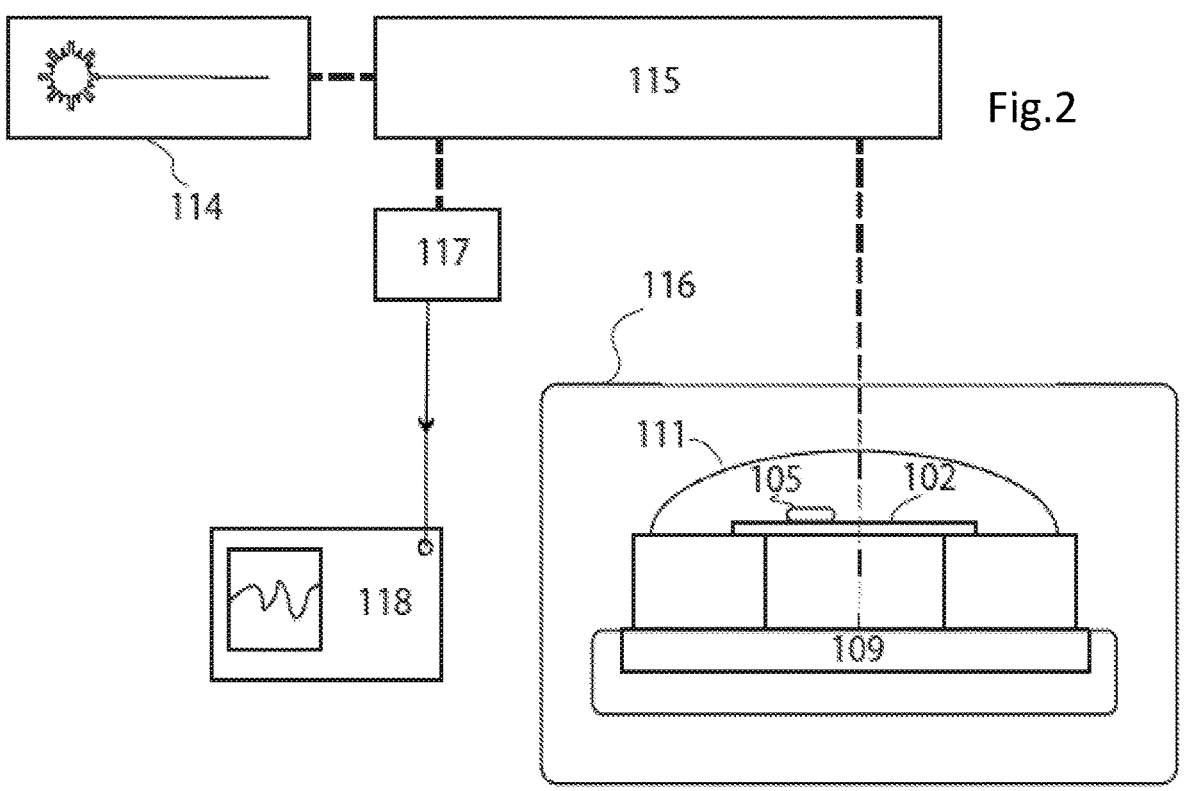
FIG. 2 is a schematic illustration of a read-out system according to an embodiment of the present invention.

FIG. 2 shows a read-out system that can be used for monitoring the metabolic activity of micro-organisms. In the embodiment of FIG. 2 a red helium-neon laser 114 is directed through optical components 115 on the 2D material layer 102 which is placed in a controlled humidity chamber 116. The intensity of the reflected light from the chip 109 is altered by the motion of the micro-organism 105 in the liquid droplet 111 that in turn moves the suspended 2D material 102. This intensity is then measured by a photo-diode 117 connected to an oscilloscope 118.

In one example a liquid droplet 111 containing micro-organism *E. coli* bacteria 105 and nutrition Lysogeny broth solution 112 has been dispensed on the sample receiver 101 comprising an array of single layer chemical vapour deposited graphene as the inert suspended layer 102. The motion is read out using the measurement system described in FIG. 2. The motion of the suspended layer is traced in a timeframe of a few seconds in the presence and absence of chemicals 113 and micro-organisms 105.

Figures 3A, 3B, 3C:
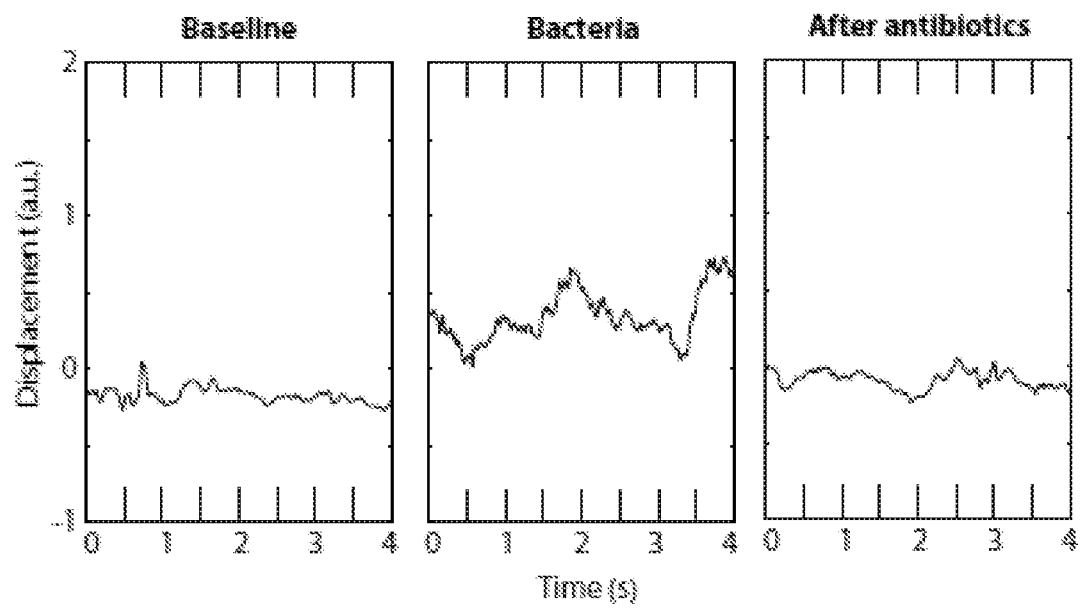
FIGS. 3a, 3b, 3c and 3d are a series of graphs or plots illustrating results of an embodiment of the present invention, FIG. 3a showing the motion of the 2d material in the presence of a droplet mixed with only nutrition, FIG. 3b showing the motion after adding bacteria, FIG. 3c showing the motion after addition of Chloramphenicol antibiotic and FIG. 3d showing the variance of the time traces given in FIGS. 3a, 3b and 3c.

FIG. 3a shows the motion of the 2D material in the presence of the droplet 111 mixed with only the nutrition 112. This trace shows almost no fluctuations, indicating the absence of bacteria.

FIG. 3b shows the motion after adding bacteria 105. This trace shows large fluctuations associated with the metabolic activity of the bacteria.

FIG. 3c shows the motion after addition of Chloramphenicol antibiotic 113 that kills the bacteria. No fluctuations are observed as a result of no bacterial metabolic activity.

Figure 3D:
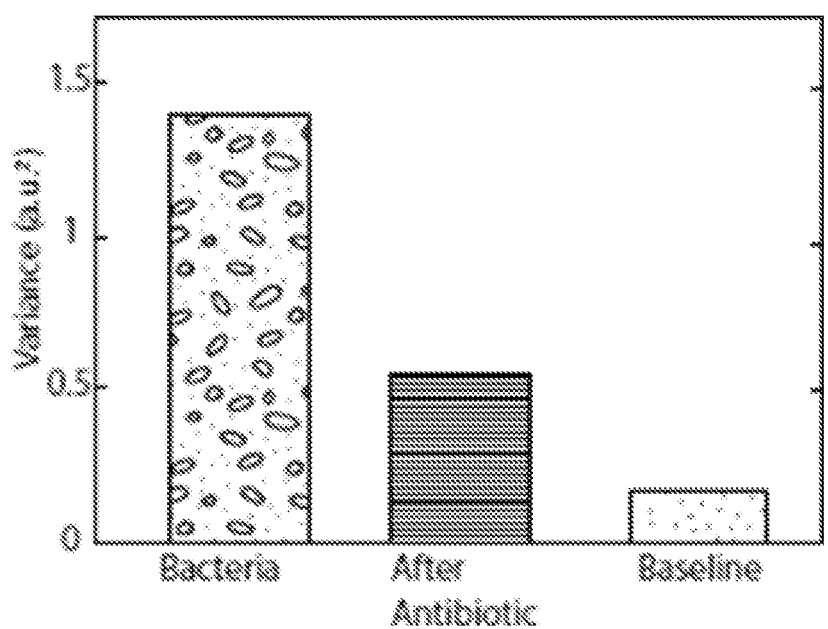

FIG. 3d Shows the variance of the time traces given in FIGS. 3a, 3b and 3c. It can be observed that the variance drops about three times after adding antibiotic to the droplet.

Figures 4A, 4B, 4C:
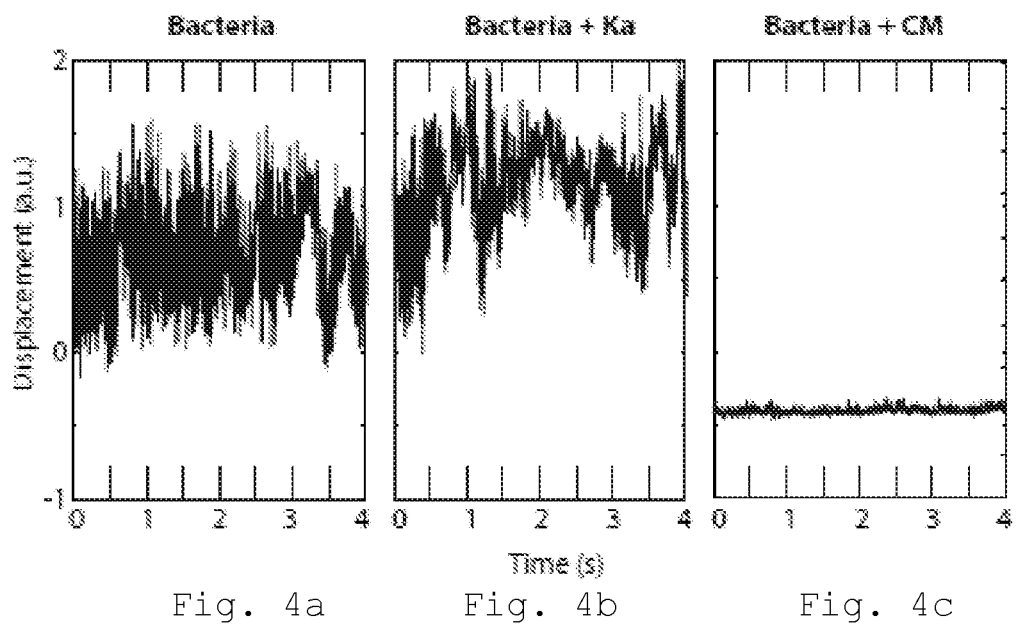
FIGS. 4a, 4b, 4c, and 4d are a series of graphs or plots illustrating results of an embodiment of the present invention.

In another example a liquid droplet 111 containing micro-organism *E. coli* bacteria 105 and nutrition Lysogeny broth solution 112 has been dispensed on the sample receiver 101 comprising an array of silanized natural crystal exfoliated 10 nm few layer thick graphene as the suspended material 102. FIGS. 4a, 4b and 4c show the time traces of the suspended layer in a timeframe of twelve minutes.

FIG. 4a shows the motion of the suspended layer with adhered bacteria 105. This time trace shows large fluctuations associated with the metabolic activity of the bacteria FIG. 4b shows the motion after addition of Kanamycin antibiotic 113 to which the micro-organism is resistant. No change in the fluctuations is observed as a result antibiotic resistance.

Figure 4D:
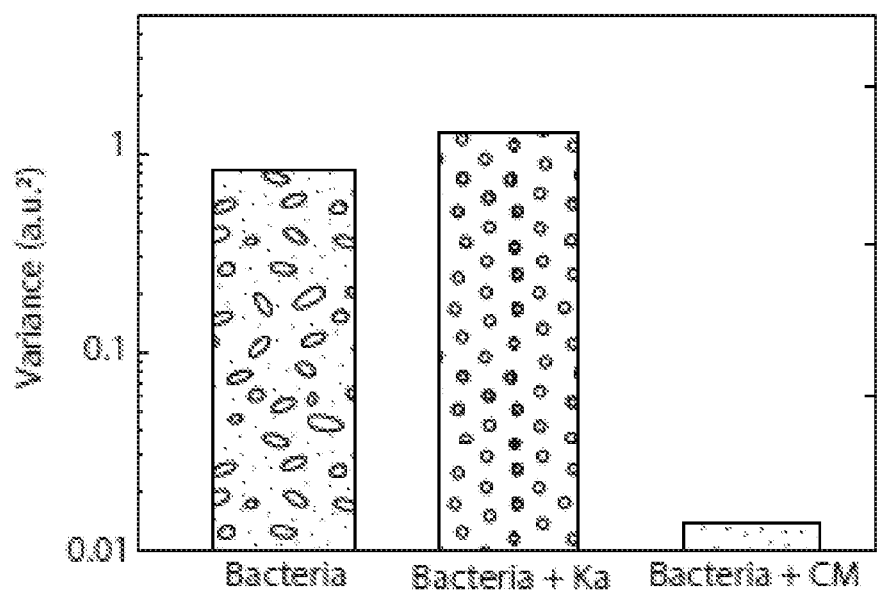

FIG. 4c shows the motion after addition of Chloramphenicol (CM) antibiotic 113 that kills the bacteria. No fluctuations are observed as a result of no metabolic activity of the bacteria FIG. 4*d* Shows the variance of the time traces given in FIGS. 4*a*, 4*b* and 4*c*. It can be observed that the variance drops about hundred times after adding Chloramphenicol to the droplet. However, almost no change in the variance is observed after adding Kanamycin (Ka).

Figure 5A:
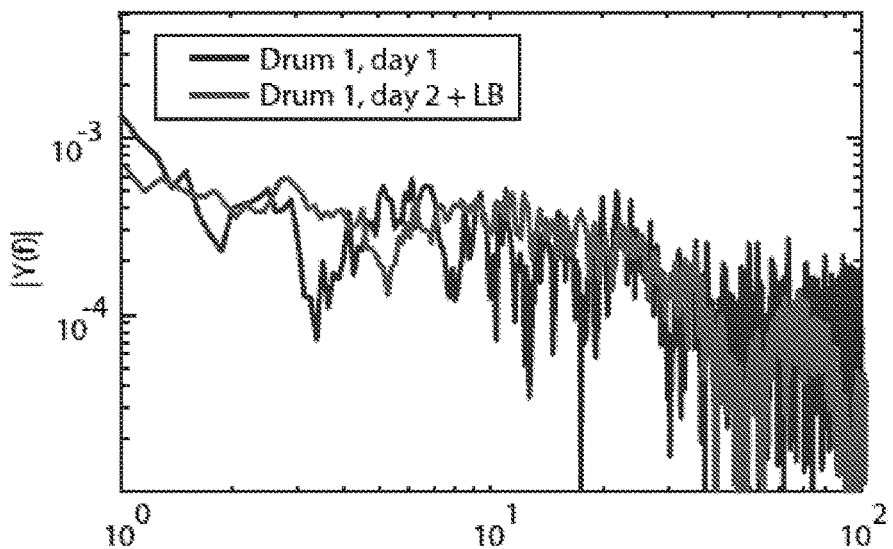
FIGS. 5a and 5b are graphs or plots of the amplitude spectra of the time traces associated with FIGS. 4a and 4c.
Figure 5B:
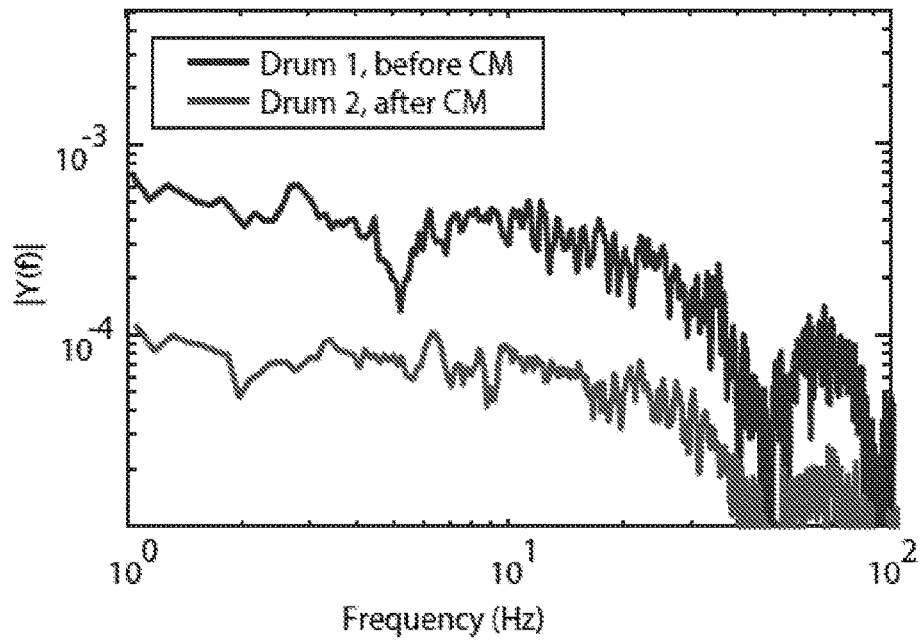

FIGS. 5*a-b* show the amplitude spectra of the time traces associated with FIG. 4*a* and FIG. 4*c*. A tenfold decrease is observed in the average amplitude of the spectrum after adding Chloramphenicol antibiotic to the droplet containing *E. coli* bacteria.

Figure 6:
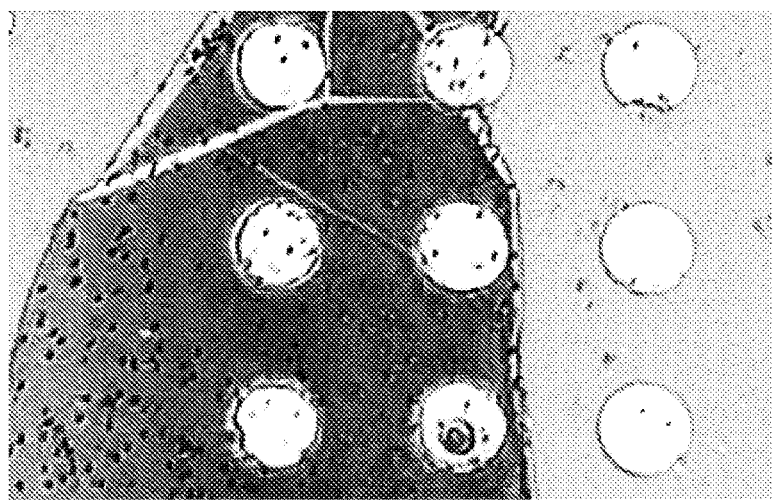
FIG. 6 is an optical microscope image of an array of silanized natural crystal exfoliated 10 nm few layer thick graphene as the suspended material in the presence of *E. coli*.

FIG. 6 shows an optical microscope image of an array of silanized natural crystal exfoliated 10 nm few layer thick graphene as the suspended material in the presence of *E. coli*. Only few bacteria can be observed per drum.

Although the invention has been discussed in the foregoing with reference to exemplary embodiments of the sensor assembly and method of the invention, the invention is not restricted to these particular embodiments which can be varied in many ways without departing from the invention. The discussed exemplary embodiments shall therefore not be used to construe the appended claims strictly in accordance therewith. On the contrary the embodiments are merely intended to explain the wording of the appended claims without intent to limit the claims to these exemplary embodiments. The scope of protection of the invention shall therefore be construed in accordance with the appended claims only, wherein a possible ambiguity in the wording of the claims shall be resolved using these exemplary embodiments.

Note that in the specification and claims, "about" or "approximately" means within twenty percent (20%) of the numerical amount cited.

Embodiments of the present invention can include every combination of features that are disclosed herein independently from each other. Although the invention has been described in detail with particular reference to the disclosed embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference. Unless specifically stated as being "essential" above, none of the various components or the interrelationship thereof are essential to the operation of the invention. Rather, desirable results can be achieved by substituting various components and/or reconfiguration of their relationships with one another.

The invention claimed is:

1. A sensor assembly for motion detection of a sample, wherein the sample is selected from a microorganism, or a living cell constituent, and a living nano-organism, the sensor assembly comprising:
    a 2D microscale motion detector adapted to act as a sample receiver, for receiving a volume of liquid, the volume being <10 µl, comprising an inert suspended layer, wherein the suspended layer is 1-5 atoms thick;
    at least one support for the suspended layer; and
    a read-out system adapted for measuring motion of the suspended layer.

2. The sensor assembly according to claim 1, wherein:
    material of the suspended layer is a two-dimensional crystal providing interlayer van der Waals interactions in a direction perpendicular to the layer surface, and comprises one of graphene, hexagonal-BN, black phosphorus, and transition metal dichalcogenides;
    the transition metal of the transition metal dichalcogenide comprises Mo, W, or Nb;
    the chalcogen of the transition metal dichalcogenide comprises S, Se and Te, MoS2, NbSe2, or WSe2, and combinations thereof.

3. The sensor assembly according to claim 1, wherein the read-out system comprises at least one of a Fabry-Perot interferometer, a Michelson interferometer, an optical interferometer, a laser Doppler vibrometer, one or more capacitor electrodes, a piezoelectrical element, a piezoresistive element, an impedance analyser; and wherein motion of the suspended layer changes the deflection, resonance frequency, reflection spectrum, transmission spectrum, optical adsorption, orientation of at least part of the suspended layer, optical interference, 2D crystal structure, electromagnetic properties, resistivity, conductivity, or any other physical characteristic or combinations thereof.

4. The sensor assembly according to claim 3, the read-out system further comprising:
    a laser for providing light;
    a first optical system for directing light from the laser to the sample;
    a second optical system for directing reflected light from the sample to a photo detector; and
    a recorder for representing motion.

5. The sensor assembly of claim 4, wherein the photo detector is a photo diode.

6. The sensor assembly of claim 4, further comprising an amplifier for amplifying detected light response.

7. The sensor assembly of claim 4, wherein the recorder comprises an oscilloscope.

8. The sensor assembly according to claim 1, wherein:
    the suspended layer is about 1-3 atoms thick;
    the suspended layer is about 0.1-50 µm wide; and
    the suspended layer is about 0.1-50 µm broad.

9. The sensor assembly according to claim 1, wherein:
    the suspended layer has a stiffness of about <10 N/m;
    the suspended layer has a Youngs modulus of about >100 GPa;
    the suspended layer has a weight of about $<10^{-15}$ kg; and
    a cavity of about >100 nm height is disposed under the suspended layer and the cavity comprises a fluid;
    the at least one support comprises an electrically insulating material comprising an electrical conductivity σ at 20° C. of about $<10^{-3}$ S/m;
    the at least one support has a height of about 20-1000 nm;
    the at least one support is provided on a substrate; and
    the suspended layer, the at least one support, and the substrate, are each individually non-toxic, and at least partly support organism activity.

10. The sensor assembly according to claim 9, wherein:
    the suspended layer has a stiffness of about <1 N/m;
    the suspended layer has a Youngs modulus of about >500 GPa according to ASTM E1111;
    the suspended layer has a weight of about $<10^{-16}$ kg;
    a fluid of a cavity under the suspended layer is a gas or liquid;
    an electrically insulating material comprises silicon oxide, silicon nitride, or silicon carbide; and
    the at least one support has a height of about 100-300 nm.

11. The sensor assembly according to claim 1, further comprising a humidity chamber for receiving the suspended layer and a sample.

12. The sensor assembly according to claim 1, comprising an array of sample receivers.

13. The sensor assembly according to claim 1, wherein the suspended layer is about 1-2 µm wide, and about 1-2 µm broad.

14. A chip comprising at least one 2D microscale motion detector according to claim 1.

15. A sensor assembly comprising a chip according to claim 14.

16. An electronic device comprising a sensor assembly according to claim 1, and further comprising:
 at least two channels each individually in electrical connection with the read-out system; and
 at least one readout line.

17. A method for operating the sensor assembly according to claim 1, the method comprising:
 providing a volume of liquid, the volume being about <10 µl, the volume comprising a microorganism, living cell constituent, or living nano-organism; and
 measuring motion of the microorganism, living cell constituent, over time.

18. The method according to claim 17, further comprising:
 adding a chemical, wherein the chemical comprises pharmaceuticals, potential pharmaceuticals, anti-biotics, kanamycin, or chloramphenicol; and
 measuring a response of the microorganism, living cell constituent, to the chemical over time.

19. The method according to claim 17, wherein the liquid comprises nutrition for the microorganism or for the living cell constituent, a physiological acceptable liquid, or a metabolic support compound.

20. A disposable sample stage for a sensor assembly according to claim 1 comprising:
 a 2D microscale motion detector adapted to act as a sample receiver, comprising an inert suspended layer, wherein the suspended layer is 1-5 atoms thick; and
 at least one support for the suspended layer.

* * * * *